(12) United States Patent
Okamoto et al.

(10) Patent No.: US 10,426,900 B2
(45) Date of Patent: Oct. 1, 2019

(54) AUTOMATIC INJECTION DEVICE

(71) Applicant: TERUMO KABUSHIKI KAISHA, Shibuya-ku, Tokyo (JP)

(72) Inventors: Kazuo Okamoto, Isehara (JP); Nozomi Ami, Hadano (JP); Tadakatsu Isozaki, Hiratsuka (JP); Daichi Kurihara, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 730 days.

(21) Appl. No.: 14/985,952

(22) Filed: Dec. 31, 2015

(65) Prior Publication Data

US 2016/0193430 A1 Jul. 7, 2016

Related U.S. Application Data

(63) Continuation of application No. 14/389,148, filed as application No. PCT/JP2013/058263 on Mar. 22, 2013, now abandoned.

(30) Foreign Application Priority Data

Mar. 22, 2012 (JP) ................................ 2012-065373

(51) Int. Cl.
*A61B 5/00* (2006.01)
*A61M 5/46* (2006.01)
(Continued)

(52) U.S. Cl.
CPC ............. *A61M 5/46* (2013.01); *A61B 5/4827* (2013.01); *A61M 5/1452* (2013.01);
(Continued)

(58) Field of Classification Search
None
See application file for complete search history.

(56) References Cited

U.S. PATENT DOCUMENTS 5,387,231 A * 2/1995 Sporer ............... A61N 1/36003
607/48
5,478,316 A 12/1995 Bitdinger et al.
(Continued)

FOREIGN PATENT DOCUMENTS

| EP | 1 349 590 B1 | 5/2006 |
|---|---|---|
| JP | 62-192141 A | 8/1987 |

(Continued)

OTHER PUBLICATIONS

Ando et al. ("Characteristics of propofol-evoked vascular pain in anaesthetized rats" British Journal of Anaesthesia, 95 (3), 2005, pp. 384-392).*

(Continued)

*Primary Examiner* — Max F Hindenburg
(74) *Attorney, Agent, or Firm* — Buchanan Ingersoll & Rooney PC (57) ABSTRACT

A method for measuring an amount of pain involves positioning a needle adjacent a non-human animal which is under anesthesia, inserting the needle at a controlled puncture speed into skin of the non-human animal, and measuring a muscle action potential of a muscle portion of the non-human animal produced by the insertion of the needle. The muscle action potential is measured from insertion start, at which the insertion of the needle into the skin is started, to insertion stop, at which the insertion of the needle into the skin is stopped.

9 Claims, 5 Drawing Sheets

(51) Int. Cl.

| | |
|---|---|
| *A61M 5/20* | (2006.01) |
| *A61M 5/145* | (2006.01) |
| *A61M 5/158* | (2006.01) |
| *A61M 5/172* | (2006.01) |
| *A61M 5/48* | (2006.01) |
| *A61M 5/315* | (2006.01) |
| *A61B 5/0488* | (2006.01) |
| *A61M 5/32* | (2006.01) |

(52) U.S. Cl.
CPC ............ *A61M 5/158* (2013.01); *A61M 5/172* (2013.01); *A61M 5/20* (2013.01); *A61B 5/0488* (2013.01); *A61B 5/4848* (2013.01); *A61B 2503/40* (2013.01); *A61B 2503/42* (2013.01); *A61M 5/31546* (2013.01); *A61M 5/326* (2013.01); *A61M 5/482* (2013.01); *A61M 2005/1585* (2013.01); *A61M 2005/206* (2013.01); *A61M 2005/31588* (2013.01); *A61M 2205/103* (2013.01); *A61M 2205/50* (2013.01)

(56) References Cited

U.S. PATENT DOCUMENTS

| | | | |
|---|---|---|---|
| 5,911,711 | A | 6/1999 | Pelkey |
| 6,356,783 | B1 | 3/2002 | Hubbard, Jr. |
| 6,678,550 | B2 * | 1/2004 | Hubbard, Jr. ........ A61B 5/0492 |
| | | | 600/546 |
| 6,890,319 | B1 | 5/2005 | Crocker |
| 2005/0197650 | A1 | 9/2005 | Sugimoto |
| 2009/0204103 | A1 | 8/2009 | Mendez |
| 2010/0049278 | A1 | 2/2010 | Kuramori |
| 2010/0063444 | A1 | 3/2010 | Wikner |
| 2011/0201998 | A1 | 8/2011 | Pongpairochana et al. |
| 2011/0224616 | A1 | 9/2011 | Slate |
| 2011/0230833 | A1 | 9/2011 | Landman et al. |
| 2012/0101439 | A9 | 4/2012 | Slate |

FOREIGN PATENT DOCUMENTS

| | | | |
|---|---|---|---|
| JP | 2000024108 | A | 1/2000 |
| JP | 20020522170 | A | 7/2002 |
| JP | 2005245852 | A | 9/2005 |
| JP | 2008125599 | A | 6/2008 |
| JP | 2010-521260 | A | 6/2010 |
| JP | 2011520569 | A | 7/2011 |
| JP | 2012020164 | A | 2/2012 |
| JP | 2012-050847 | A | 3/2012 |
| WO | WO 02/074367 | A2 | 9/2002 |
| WO | WO 2005/077441 | A2 | 8/2005 |
| WO | 2009/041110 | A1 | 4/2009 |
| WO | WO 2009/143255 | A1 | 11/2009 |

OTHER PUBLICATIONS

Aoyagi et al. ("Biodegradable polymer needle with various tip angles and consideration on insertion mechanism of mosquito's proboscis" Sensors and Actuators A: Physical, vol. 143, Issue 1, May 2, 2008, pp. 20-28).*
Xie et al. ("The Common Inhalation Anesthetic Isoflurane Induces Caspase Activation and Increases Amyloid (β-Protein Level in Vivo" Annals of neurology, vol. 64 (6), 2008, pp. 618-627).*
Zbinden et al. ("Anesthetic Depth Defined Using Multiple Noxious Stimuli during Isoflurane/Oxygen Anesthesia" II. Hemodynamic Responses, Anesthesiology, 80(2), 1994, pp. 261-267).*
Daube et al. ("Needle Electromyography" Muscle Nerve, 39, 2009, pp. 244-270).*
Office Action (Notification of Reasons for Refusal) dated Oct. 25, 2016 by the Japanese Patent Office in corresponding Japanese Patent Application No. 2015-065129 and a partial English translation thereof. (5 pgs).
Office Action (Notification of Reasons for Refusal) dated Nov. 8, 2016 by the Japanese Patent Office in corresponding Japanese Patent Application No. 2014-506295 and a partial English translation thereof. (6 pgs).
International Search Report (PCT/ISA/210) dated Apr. 23, 2013, by the Japanese Patent Office as the International Searching Authority for International Application No. PCT/JP2013/058263.
Written Opinion (PCT/ISA/237) dated Apr. 23, 2013, by the Japanese Patent Office as the International Searching Authority for International Application No. PCT/JP2013/058263.
European Search Report dated Oct. 26, 2015, by the European Patent Office in corresponding European Patent Application No. 13763919.1-1662. (6 pages).
European Search Report dated Oct. 22, 2015, by the European Patent Office in corresponding European Patent Application No. 15168572.4-1662. (5 pages).

* cited by examiner

AUTOMATIC INJECTION DEVICE

This application is a continuation of U.S. application Ser. No. 14/389,148 filed on Feb. 4, 2015, which is a U.S. national stage application based on International Application No. PCT/JP2013/058263 having an international filing date of Mar. 22, 2013, and claims priority to Japanese Application No. 2012-065373 filed on Mar. 22, 2012, the entire content of all three of which is incorporated herein by reference.

TECHNICAL FIELD

The present invention relates to an automatic injection device for moving a syringe held in the main body at a high speed to automatically perform puncture/injection.

BACKGROUND DISCUSSION

Presently, as medicaments, use of protein preparations such as molecular targeting drugs, vaccines, and hormonal agents typified by insulin rapidly increases, and a device capable of easy administration of these medicaments is required. These medicaments are a high-molecular protein or peptide and are not absorbed into a body through oral administration. Therefore, administration by a syringe needle into a hypodermis or blood vessel is necessary.

Administration by a syringe needle, such as hypodermic, intravenous, and intramuscular administrations, is a general administration method presently. However, a drug solution is infused through puncture by the syringe needle and thus this method involves pain when the needle penetrates the skin. Therefore, in some cases, fear of the pain when puncture by a syringe needle is performed and discomfort in infusion of a drug solution is caused in a patient to which the drug solution is administered by using a syringe and the patient refuses the drug treatment or becomes negative about it. This leads to delay in the treatment. In particular, diabetes patients for which insulin injection is necessary and patients with growth deficiency for which growth hormone injection is necessary are frequently children, and the pain and discomfort in injection are also a cause of later "injection phobia" (Needle phobia).

Therefore, for patients including such child patients, a device that can be easily operated in injection and does not involve pain and allows automatic injection without direct contact with a syringe needle and a syringe is desired.

To meet this desire, as an automatic injection device that enables a patient to personally administer a drug solution easily, devices that automatically perform puncture and infusion by pressing a syringe and a pusher (plunger) of the syringe by a spring force have been proposed.

For example, the following device is described in Patent Document 1. The device includes a drive assembly and a syringe assembly mounted to the drive assembly. The drive assembly includes a drive rod, a driver releasably coupled to the drive rod, and a constant force spring that urges the drive rod toward the syringe assembly. In this device, the spring urges the coupled drive rod and driver along the axis line of the device to puncture the skin by a needle of the syringe assembly. Then, the drive rod is decoupled from the driver and the spring continues to urge the drive rod in the axis line direction. Thereby, the drive rod engages with a piston in the syringe assembly and pushes out a medicament therein to automatically perform an injection.

Furthermore, the following device is described in Patent Document 2. The device includes a housing that is so configured as to internally contain a medicament container. The housing includes a contact part to be applied to an injection site, a needle cover that surrounds a needle disposed to the medicament container and extends by at least the length of the needle, spring means capable of, when being actuated, pushing the needle to make it pass through an end part of the needle cover and operating the medicament container to supply a dose of medicament. The housing further includes first locking means capable of locking the spring means in a pressurized state and first actuating means capable of releasing the spring means for an injection when being manually operated. In this device, by pressing a button, a syringe to which the spring is mounted is actuated and the medicament is automatically injected.

Moreover, the following device is described in Patent Document 3. The device includes an elongated housing, a container containing a medicament to be infused through a needle, pressurizing means that acts on the container and is capable of, when being actuated, moving the container and the needle for puncture and subsequently expelling the medicament through the needle, and actuating means disposed to actuate the pressurizing means. In this device, the actuating means includes a needle shield disposed slidably relative to the housing and a collapsible holding member connected to an inner end part of the needle shield. Due to this, in the movement of the needle shield, the collapsible holding member collapses when a certain force is applied by the needle shield. Thereby, the further movement of the needle shield actuates the actuating means. Then, the actuating means releases the pressurizing means to initiate infusion of the medicament.

PRIOR ART DOCUMENTS

Patent Documents

Patent Document 1: U.S. Pat. No. 5,478,316
Patent Document 2: EP Patent No. 1,349,590
Patent Document 3: JP 2010-521260 A

SUMMARY

The devices described in Patent Documents 1 to 3 are devices with which a series of action of punctuating the skin by a syringe needle and infusing a drug solution and then withdrawing the syringe needle can be automatically performed. However, they do not alleviate pain accompanying the puncture by the syringe needle and the infusion of the drug solution.

With a device that presses a syringe and a plunger by using a spring to automatically perform puncture and infusion of a drug solution like the devices described in Patent Documents 1 to 3, high-speed puncture based on the repulsive force of the spring is performed and thus an impact on the skin (vibration, feeling of pressure, impact sound, etc.) is made at the time of the puncture, giving anxiety and fear about the injection to the patient. Furthermore, because the puncture and infusion are performed by the same spring, it is difficult to set conditions in detail about the puncture speed, the puncture depth, and the infusion rate of the drug solution depending on the patient and the kind of medicament.

Furthermore, in the dental field, an electric infusion instrument that automatically infuses a drug solution at a constant speed is used as an instrument to administer anesthetic. However, puncture by a syringe needle is performed by an operator and the puncture is not automatically performed.

Moreover, to alleviate pain in puncture, a syringe needle whose diameter is set small is developed and is used in a clinical scene. However, in administration of a large amount of medicament and administration of a medicament having a high viscosity, the infusion resistance is high and a long time is taken.

The automatic injection device disclosed here automatically performs puncture and allows setting of conditions of the puncture according to the thickness of a syringe needle, the puncture depth, and so forth. Furthermore, the automatic injection device reduces pain in puncture and in drug solution infusion and reduces the impact in the puncture to allow alleviation of anxiety and fear of a patient.

The automatic injection device can automatically perform puncture with very little pain of the puncture at such a puncture speed as to yield almost no pain.

The automatic injection device performs puncture by causing an advance of a syringe having a distal end at which a syringe needle is disposed. The automatic injection device has a syringe holder that holds the syringe attachably and detachably, a first drive unit that causes the syringe holder holding the syringe to advance to perform puncture by the syringe needle, and a control unit that controls the first drive unit to control a puncture speed.

Here, it is preferable that the first drive unit includes a first electric motor and a first motion converter that converts rotational motion of the first electric motor to linear motion and causes the syringe holder to advance.

Furthermore, it is preferable that the thickness of the syringe needle of the syringe is in a range of 18 G to 34 G and the puncture speed in puncture with the syringe needle by the first drive unit satisfies 10 to 500 mm/s.

In addition, it is preferable to employ the following configuration. Specifically, the syringe has, in addition to the syringe needle, a syringe barrel filled with a drug solution and a plunger for infusing the drug solution in the syringe barrel into a subject from the syringe needle with which puncture is performed. The automatic injection device has a second drive unit that causes the plunger to advance to infuse the drug solution. The control unit controls the second drive unit to infuse the drug solution at a predetermined infusion rate after puncture by the first drive unit.

Moreover, it is preferable that the second drive unit includes a second electric motor and a second motion converter that converts rotational motion of the second electric motor to linear motion.

Furthermore, it is preferable that the first drive unit moves the second drive unit and the syringe holder integrally.

In addition, it is preferable that the control unit controls the infusion rate of the drug solution by the second drive unit to 1 to 1000 μL/s.

Moreover, it is preferable that the control unit controls the first drive unit so that the puncture depth when the first drive unit causes the syringe holder to advance to perform puncture with the syringe needle is a depth of 1 to 50 mm.

Furthermore, it is preferable that the control unit controls the first drive unit to cause the syringe holder to retreat and withdraw the syringe needle after elapse of a predetermined stop time after drug solution infusion by the second drive unit.

In addition, it is preferable that the control unit variably controls a puncture speed in the middle of puncture in the puncture with the syringe needle by the first drive unit.

In automatically performing puncture, conditions of the puncture can be set according to the thickness of a syringe needle, the puncture depth, and so forth. This reduces pain in the puncture and reduces the impact in the puncture, allowing alleviation of anxiety and fear of a patient.

Furthermore, according to a preferred mode, the puncture speed in puncture by the first drive unit satisfies 10 to 500 mm/s when the thickness of the syringe needle is in a range of 18 G to 34 G. This can automatically perform puncture with very little pain of the puncture at such a puncture speed as to yield almost no pain.

Another aspect of the disclosure here involves a method for measuring an amount of pain. The method involves positioning a needle adjacent a non-human animal which is under anesthesia, inserting the needle at a controlled puncture speed into skin of the non-human animal, and measuring a muscle action potential of a muscle portion of the non-human animal produced by the insertion of the needle. The muscle action potential is measured from insertion start, at which the insertion of the needle into the skin is started, to insertion stop, at which the insertion of the needle into the skin is stopped.

Another aspect involves a method comprising: positioning a needle adjacent a non-human animal which is anesthetized, with the needle being a first-size needle possessing a first outer diameter; inserting the first-size needle at a first controlled puncture speed into the non-human animal through skin of the non-human animal; measuring penetration resistance of the insertion of the first-size needle at the first controlled puncture speed from insertion start, at which the insertion of the first-sized needle into the skin is started, to insertion stop, at which the insertion of the first-size needle into the skin is stopped; measuring an amount of pain during the insertion of the first-size needle at the first controlled puncture speed; and inserting a needle at a second controlled puncture speed into the non-human animal through skin of the non-human animal, with the second controlled puncture speed being different from the first controlled puncture speed, and the needle inserted at the second controlled puncture speed being a first-size needle possessing the first outer diameter. The method also includes: measuring penetration resistance of the insertion of the first-size needle at the second controlled puncture speed from insertion start, at which the insertion of the first-size needle into the skin is started, to insertion stop, at which the insertion of the needle into the skin is stopped; measuring an amount of pain during the insertion of the first-size needle at the second controlled puncture speed; and using results of the measured penetration resistance and the measured amount of pain to select either the first controlled puncture speed or the second controlled puncture speed to reduce pain of the non-human animal resulting from the insertion.

In accordance with another aspect, a method comprises: positioning a needle adjacent a non-human animal which is anesthetized, the needle being a first-size needle possessing a first outer diameter; inserting the first-size needle at a first controlled puncture speed into the non-human animal through skin of the non-human animal; measuring penetration resistance of the insertion of the first-size needle at the first controlled puncture speed from insertion start, at which the insertion of the first-sized needle into the skin is started, to insertion stop, at which the insertion of the first-size needle into the skin is stopped; measuring an amount of pain during the insertion of the first-size needle at the first controlled puncture speed; and inserting a needle, which is different from the first-size needle, at the first controlled puncture speed into the non-human animal through skin of the non-human animal, wherein the needle which is different from the first-size needle is a second-size needle possessing a second outer diameter different from the first outer diameter. The method additionally includes measuring penetration resistance of the insertion of the second-size needle at the first controlled puncture speed from insertion start, at which the insertion of the second-size needle into the skin is started, to insertion stop, at which the insertion of the second-size needle into the skin is stopped; measuring an amount of pain during the insertion of the second-size needle at the first controlled puncture speed; and using results of the measured penetration resistance and the measured amount of pain to select either the first-size needle or the second-size needle to reduce pain of the non-human animal resulting from the insertion.

A still further aspect of the disclosure here involves a method comprising: inserting different-size needles, which possess different outer diameters, at different controlled puncture speeds into an anesthetized non-human animal through skin of the anesthetized non-human animal; measuring penetration resistance of the insertion of the different-size needles at the different controlled puncture speeds from insertion start, at which the insertion of each respective different-size needle into the skin is started, to insertion stop, at which the insertion of each respective different-size needle into the skin is stopped; measuring an amount of pain during the insertion of the different-size needles at the different controlled puncture speeds; and using results of the measured penetration resistance and the measured amount of pain to select one of the different-size needles and one of the different controlled puncture speeds to reduce pain of the non-human animal resulting from the insertion.

DETAILED DESCRIPTION

An automatic injection device according to the present invention will be described in detail below based on a preferred embodiment shown in the accompanying drawings.

Figure 1:
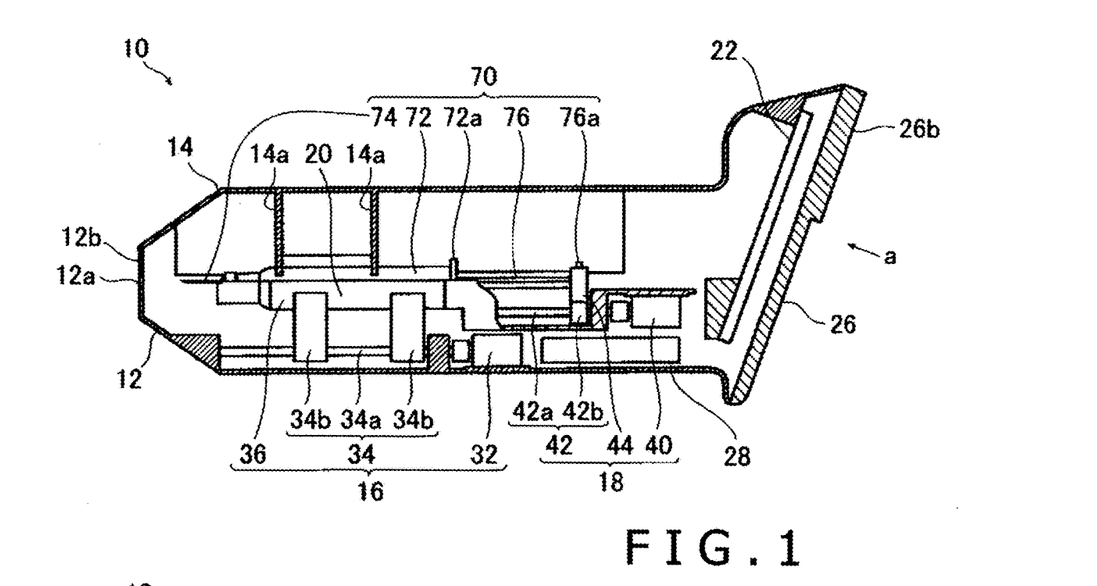
FIG. 1 is a sectional view conceptually showing one embodiment of an automatic injection device of the present invention.
Figure 2:
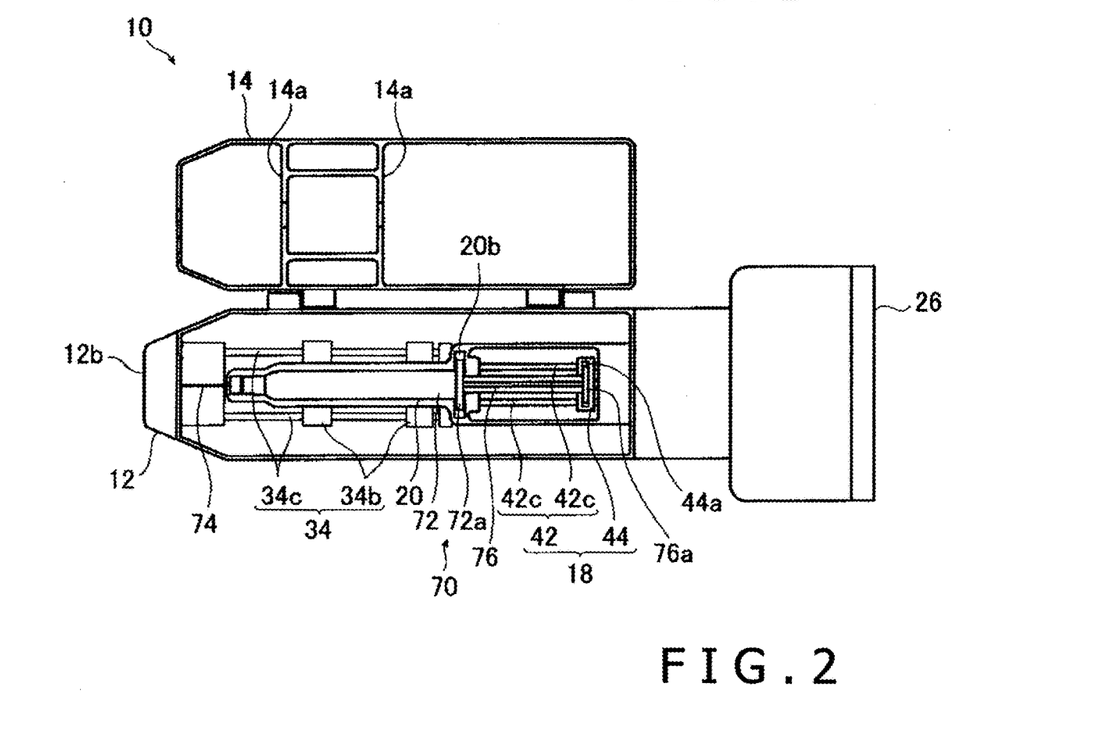
FIG. 2 is a front view of the automatic injection device shown in FIG. 1.

FIG. 1 is a sectional view showing the outline of the automatic injection device according to the present invention and FIG. 2 is a front view of a state in which a cover 14 of an automatic injection device 10 shown in FIG. 1 is opened.

Figure 3:
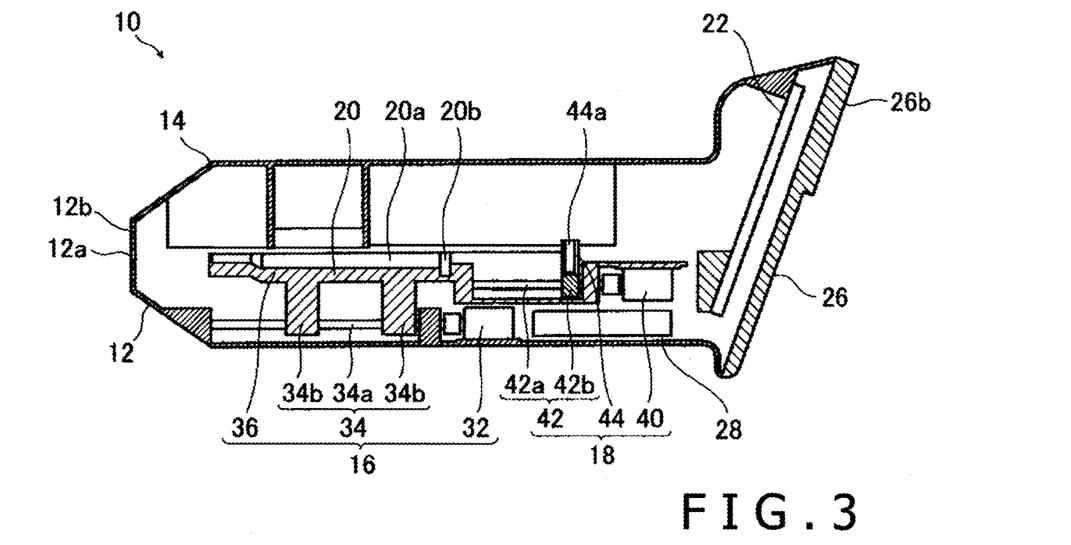
FIG. 3 is a sectional view of the automatic injection device in a state in which a syringe is not mounted therein.

Furthermore, FIG. 3 is a schematic sectional view of the automatic injection device 10 in a state in which a syringe 70 is removed.

The syringe 70 mounted in the automatic injection device 10 is a normal syringe having a syringe barrel 72 that is internally filled with a drug solution and has a cylindrical shape, a syringe needle 74 that is disposed at the distal end of the syringe barrel 72 to be inserted into the body of a subject (patient) and expels the drug solution from the distal end, and a plunger 76 for expelling the drug solution in the syringe barrel 72 from the syringe needle 74. The plunger 76 includes a piston part that is inserted into the syringe barrel 72 from the opposite side to the side of the syringe needle 74 (proximal side) and is slidable in the syringe barrel 72.

In the example shown in the diagrams, a flange 72a locked into a locking groove 20b of a syringe holder 20 to be described later is provided on the proximal side of the syringe barrel 72.

Furthermore, a flange 76a locked into a locking groove 44a of a pressing member 44 to be described later is provided on the proximal side of the plunger 76.

Note that the syringe 70 may be filled with a drug solution by an operator or may be a pre-filled syringe filled with a drug solution in advance.

The automatic injection device 10 is a device that automatically performs injection through mounting of the syringe 70 in a housing 12. The automatic injection device 10 has the housing 12, the cover 14, a first drive unit 16 for performing puncture by the syringe needle 74 of the syringe 70, a second drive unit 18 for performing infusion of a drug solution by the syringe 70, the syringe holder 20, a control unit 22 that controls the first drive unit 16 and the second drive unit 18, an operation unit 26, and a battery 28 that supplies the respective units with power.

The syringe holder 20 is a part that holds the syringe 70 with the longitudinal direction of the syringe 70 set identical to the direction of driving by the first drive unit 16 to be described later.

As shown in FIGS. 2 and 3, the syringe holder 20 has, along the longitudinal direction of the syringe 70, a recess 20a that corresponds to the shape of the syringe barrel 72 of the syringe 70 and has a semicircular shape in section perpendicular to the longitudinal direction. Furthermore, the locking groove 20b for locking of the flange 72a of the syringe barrel 72 is formed on the proximal side of the recess 20a (on the side of the plunger 76).

Note that, in the example shown in the diagrams, the syringe holder 20 is formed monolithically with blocks 34b and a base 36 of the first drive unit 16 to be described later.

The first drive unit 16 is a part for moving the syringe holder 20 on which the syringe 70 is placed toward the syringe needle 74 in the longitudinal direction of the syringe 70 and performing puncture with the syringe needle 74 disposed at the distal end of the syringe 70.

Note that, in the following description, the case of moving the syringe holder 20 with the syringe 70 placed thereon toward the syringe needle 74 is defined as an advance and the case of moving the syringe holder 20 toward the plunger 76 is defined as retreat.

The first drive unit 16 has a first motor 32, a first motion converter 34, and the base 36.

The first motor 32 is a normal stepping motor that operates according to supplied power and its rotational speed and rotation amount can be controlled.

The first motor 32 rotates at a predetermined rotational speed by a predetermined rotation amount in such a direction as to cause the syringe holder 20 to advance (hereinafter, defined as the forward direction). Thereafter, after the operation is stopped during a predetermined time, the first motor 32 is controlled by the control unit 22 to be described later to rotate at a predetermined rotational speed by a predetermined rotation amount in such a direction as to cause the syringe holder 20 to retreat (hereinafter, defined as the reverse direction).

Specifically, when a start button 26a of the operation unit 26 is operated, the first motor 32 is first controlled by the control unit 22 to rotate in the forward direction by a predetermined rotation amount at a predetermined rotational speed according to operating conditions of puncture speed and puncture depth that are input by the operation unit 26 and set in advance. After the rotation by the predetermined rotation amount, the operation is temporarily stopped. The second drive unit 18 to be described later operates during the temporary stop of the first motor 32 and therefore the stop state is kept until the completion of the operation of the second drive unit 18. After the completion of the operation of the second drive unit 18 and the elapse of a predetermined stop time, the first motor 32 is controlled to rotate in the reverse direction by a predetermined rotation amount at a predetermined rotational speed according to a condition of a retreat speed (withdrawal speed) set in advance so that the syringe holder 20 may return to the original position.

The first motor 32 is connected to a screw shaft 34a of the first motion converter 34 and rotates the screw shaft 34a.

The first motion converter 34 is a so-called ball screw and is a part for converting the rotational motion of the first motor 32 to linear motion to cause the base 36 of the syringe holder 20 to advance/retreat.

The first motion converter 34 has the screw shaft 34a having a screw groove formed on its circumferential surface, two guide shafts 34c symmetrically disposed to sandwich the screw shaft 34a, and the two blocks 34b. In the blocks 34b, a female screw screwed to the screw groove of the screw shaft 34a with the intermediary of plural balls is formed and two guide holes into each of which a respective one of the two guide shafts 34c is inserted are formed.

The screw shaft 34a is rotatably supported by bearings formed on the housing 12 on both end sides. Furthermore, both end parts of the guide shafts 34c are supported by the housing 12.

Furthermore, the first motion converter 34 is disposed with the axis of the screw shaft 34a set along the longitudinal direction of the syringe 70 (syringe needle 74) and thus can move the syringe needle 74 in the puncture direction.

Moreover, the two blocks 34b are disposed at a predetermined interval in the longitudinal direction of the syringe 70.

When the first motor 32 rotates, the screw shaft 34a connected to the first motor 32 rotates. Upon the rotation of the screw shaft 34a, the two blocks 34b screwed to the screw shaft 34a advance/retreat along the axis of the screw shaft 34a. Here, because the guide shafts 34c are inserted into the guide holes of the two blocks 34b, the two blocks 34b make linear motion along the screw shaft 34a without rotating around the screw shaft 34a when the screw shaft 34a rotates.

The base 36 is fixed to the two blocks 34b of the first motion converter 34.

Note that, although a ball screw is used as the first motion converter 34 in the example shown in the diagrams, the present invention is not limited thereto and various publicly-known conversion mechanisms between rotational motion and linear motion, such as feed screw mechanism, rack and pinion mechanism, and crank mechanism, may be used.

Alternatively, a linear motor may be used instead of the first motor 32 and the first motion converter 34.

Note that it is preferable to use a ball screw as the first motion converter 34 in that the positional accuracy is high and the controllability is high and in that the friction loss is small and the energy efficiency is high.

Furthermore, although the configuration in which the first motion converter 34 has the two blocks 34b is employed, the configuration is not limited thereto and a configuration in which the first motion converter 34 has one block 34b may be employed. By disposing the two blocks 34b at a predetermined interval, the base 36 can be prevented from tilting in the front-rear direction and swinging.

The base 36 is a pedestal on which to place the syringe holder 20 and the second drive unit 18 and is fixed to the blocks 34b of the first motion converter 34.

Because being fixed to the blocks 34b of the first motion converter 34, the base 36 is made to advance/retreat along the screw shaft 34a when the first motor 32 is driven. That is, when the first motor 32 is driven, the syringe holder 20 and the second drive unit 18 are made to integrally advance/retreat.

Note that the base 36 is formed monolithically with the syringe holder 20 and the blocks 34b in the example shown in the diagrams as described above.

Here, as described above, the first motor 32 is controlled by the control unit 22 to rotate at a predetermined rotational speed by a predetermined rotation amount according to conditions such as puncture speed and puncture depth set in advance by input from the operation unit 26. Therefore, first, by the rotation of the first motor 32 in the forward direction, the syringe holder 20 linearly moves to a predetermined position at a predetermined advance speed. Thereby, puncture is performed by the syringe needle 74 of the syringe 70 to the set puncture depth at the set puncture speed.

Next, the base 36 keeps the stop state during the stop of the first motor 32. Thereafter, by the rotation of the first motor 32 in the reverse direction, the base 36 linearly moves to the original position at a predetermined retreat speed. Thereby, the syringe needle 74 of the syringe 70 is withdrawn at a predetermined withdrawal speed.

As described above, the conventional automatic injection devices are devices that press a syringe by using the repulsive force of a spring to automatically perform puncture and therefore involve a problem that an impact on the skin (vibration, feeling of pressure, impact sound, etc.) is made at the time of the puncture and anxiety and fear about the injection are given to the patient. Furthermore, because the puncture and infusion are performed by the same spring, there is a problem that it is difficult to set conditions in detail about the puncture speed and the puncture depth according to the thickness of a syringe needle, the kind of medicament, the patient, etc.

In contrast, in the automatic injection device 10 of the present invention, the first drive unit 16 to drive the syringe holder 20 is configured with the first motor 32 and the first motion converter 34 and the syringe 70 having the syringe needle 74 is held in the syringe holder 20. In the first drive unit 16, the first motor 32 rotates according to puncture speed, puncture depth, and so forth set in advance and the syringe holder 20 is made to advance through the first motion converter 34 to perform puncture with the syringe needle 74. Thus, conditions of the puncture, such as the puncture speed, can be set according to the thickness of the syringe needle, the puncture depth, the patient, and so forth and the puncture can be performed at a proper puncture speed, allowing reduction in pain in the puncture and reduction in the impact in the puncture. This can alleviate anxiety and fear of the patient.

Furthermore, the first drive unit 16 to perform the puncture is configured independently of the second drive unit 18 to infuse a drug solution. Thus, a proper puncture speed can be set regardless of operating conditions of the second drive unit 18.

Here, the advance speed when the first drive unit 16 makes the syringe holder 20 advance to perform the puncture, i.e. the puncture speed, can be appropriately set according to the thickness of the syringe needle 74 and the puncture depth or the sensitivity of the patient, the injection site, and so forth. If a syringe whose thickness of the syringe needle 74 is in a range of 18 G to 34 G is used as the syringe 70, it is preferable to set the puncture speed in a range of 10 mm/s to 500 mm/s. Furthermore, it is more preferable to set the puncture speed in a range of 25 mm/s to 500 mm/s and it is further preferable to set it in a range of 75 mm/s to 500 mm/s.

Setting the puncture speed equal to or higher than 10 mm/s can alleviate pain in the puncture and allows the puncture with the patient caused to feel almost no pain. Furthermore, setting the puncture speed equal to or lower than 500 mm/s can reduce impact and recoil at the time of the puncture and reduce anxiety and fear of the patient.

Furthermore, by setting the puncture speed in a range of 25 mm/s to 500 mm/s, nearly painless puncture can be performed. Moreover, by setting the puncture speed in a range of 75 mm/s to 500 mm/s, painless puncture in which the patient is surely prevented from feeling pain in the puncture can be performed.

A preferable range of the puncture speed will be described in detail later.

Furthermore, there is no particular limit to the retreat speed when the first drive unit 16 makes the syringe holder 20 retreat to withdraw the syringe needle 74, i.e. the withdrawal speed. However, it is preferable to set the withdrawal speed in a range of 1 to 500 mm/s.

Setting the withdrawal speed to a constant speed in the range of 1 to 500 mm/s is preferable in that the stimulus to pain sensing nerves due to the vibration of the already-inserted needle and friction with the insertion site can be alleviated and pain caused in the withdrawal can be minimized.

Furthermore, in the present embodiment, as a preferred mode, based on control by the control unit 22, the first drive unit 16 makes the syringe holder 20 retreat to withdraw the syringe needle 74 after the elapse of a predetermined stop time after the completion of infusion of a drug solution by the second drive unit 18. If the syringe needle 74 is withdrawn immediately after the infusion of the drug solution, the drug solution does not sufficiently diffuse and possibly the drug solution leaks out. Therefore, it is preferable to withdraw the syringe needle 74 after the elapse of the predetermined stop time from the completion of the infusion of the drug solution.

In the present embodiment, the stop time to the withdrawal of the syringe needle 74 can also be set through input from the operation unit 26 by an operator.

In addition, the first drive unit 16 does not only automatically carry out operation for puncture based on an input signal from the start button 26a but can cause advance/retreat at a low speed in accordance with operation of the operation unit 26. That is, an operator can manually make the first drive unit 16 cause advance/retreat by operating the operation unit 26. This allows the position of the distal end of the syringe needle 74 to be adjusted to a predetermined position after the syringe 70 is set in the syringe holder 20.

The second drive unit 18 is a part for pressing the plunger 76 of the syringe 70 in the direction of the syringe needle 74 to make it advance and expelling a drug solution in the syringe barrel 72 from the distal end of the syringe needle 74 based on control by the control unit 22.

The second drive unit 18 has a second motor 40, a second motion converter 42, and the pressing member 44.

The second motor 40 is a normal stepping motor that operates according to supplied power as with the first motor 32, and its rotational speed and rotation amount can be controlled.

The second motor 40 is controlled by the control unit 22 to rotate in the forward direction by a predetermined rotation amount at a predetermined speed according to conditions of infusion rate and infusion amount of a drug solution set in advance through input from the operation unit 26 while the first drive unit 16 temporarily stops its operation after carrying out operation of puncture.

The second motor 40 is connected to a screw shaft 42a of the second motion converter 42 and rotates the screw shaft 42a.

The second motion converter 42 is a ball screw as with the first motion converter 34. It is a part that converts rotational motion of the second motor 40 to linear motion and is to cause the plunger 76 locked to the pressing member 44 to advance/retreat.

Similarly to the first motion converter 34, the second motion converter 42 has the screw shaft 42a having a screw groove formed on its circumferential surface, two guide shafts 42c symmetrically disposed to sandwich the screw shaft 42a, and a block 42b. In the block 42b, a female screw screwed to the screw groove of the screw shaft 42a with the intermediary of plural balls is formed and two guide holes into each of which a respective one of the two guide shafts 42c is inserted are formed.

The screw shaft 42a is rotatably supported by bearings formed on the base 36 on both end sides. Furthermore, both end parts of the guide shafts 42c are supported by the base 36.

Furthermore, the second motion converter 42 is disposed with the axis of the screw shaft 42a set along the longitudinal direction of the syringe 70 and the syringe needle 74.

When the second motor 40 rotates based on control from the control unit 22, the screw shaft 42a connected to the second motor 40 rotates. Upon the rotation of the screw shaft 42a, the block 42b screwed to the screw shaft 42a advances/retreats along the axis of the screw shaft 42a. Here, because the guide shafts 42c are inserted into the guide holes of the block 42b, the block 42b makes linear motion along the screw shaft 42a without rotating around the screw shaft 42a when the screw shaft 42a rotates.

The pressing member 44 is fixed to the block 42b of the second motion converter 42.

Note that another publicly-known motion conversion mechanism may be used as the second motion converter 42 as with the first motion converter 34.

The pressing member 44 is a member for pressing the plunger 76 of the syringe 70 to make it advance and is fixed to the block 42b of the second motion converter 42.

The locking groove 44a for locking the flange 76a of the plunger 76 is formed in the pressing member 44.

Because being fixed to the block 42b of the second motion converter 42, the pressing member 44 is made to advance/retreat along the screw shaft 42a when the second motor 40 is driven.

Here, as described above, the second motor 40 is controlled by the control unit 22 to rotate at a predetermined rotational speed by a predetermined rotation amount according to conditions such as infusion rate and infusion amount set in advance by input from the operation unit 26. Therefore, by the rotation of the second motor 40 in the forward direction, the pressing member 44 is linearly moved to a predetermined position at a predetermined advance speed. Thereby, the plunger 76 of the syringe 70 is pressed and the set amount of drug solution is expelled from the distal end of the syringe needle 74 at the infusion rate set in advance.

As above, as a preferred mode of the present invention, the second drive unit 18 for infusing a drug solution is provided independently of the first drive unit 16 for performing puncture. This can set infusion rate and infusion amount regardless of set puncture speed, puncture depth, and so forth. Thus, a drug solution can be infused at the optimum infusion rate and discomfort and so forth accompanying the infusion of the drug solution can be alleviated. Furthermore, the speed of puncture by the first drive unit 16 can be set independently of the second drive unit 18. Thus, puncture can be performed at the optimum puncture speed, allowing reduction in pain in the puncture and reduction in the impact in the puncture.

Here, the infusion rate when the second drive unit 18 makes the pressing member 44 advance to infuse a drug solution can be appropriately set according to the thickness of the syringe needle 74 and the puncture depth or the kind of drug solution, the infusion amount, and so forth. It is known that the infusion rate of a drug solution and pain have a correlation and pain is less when the infusion rate is lower. What degree the optimum infusion rate is at in practice differs depending on the kind of infused medicament, the infusion amount, the infusion-target site, and so forth. Nagasawa et al. has made the following report. Specifically, Nagasawa et al. administered a physiological saline to the rat oral mucosa with variation in the infusion rate and measured pain by using electromyography. As a result, the pain was alleviated at a rate of 10 µL/s (Ikuko Nagasawa et al., J. Jpn. Dent. Soc. Anesthesiol., 31:497, 2003). On the other hand, in the case of rapid administration into a blood vessel or hypodermis, the drug solution is infused at a much higher infusion rate in practice. In view of such results, it is preferable to set the infusion rate in a range of 1 to 1000 µL/s.

Setting the infusion rate of a drug solution in the range of 1 to 1000 µL/s can reduce pain and discomfort accompanying the infusion of the drug solution.

Figure 4:
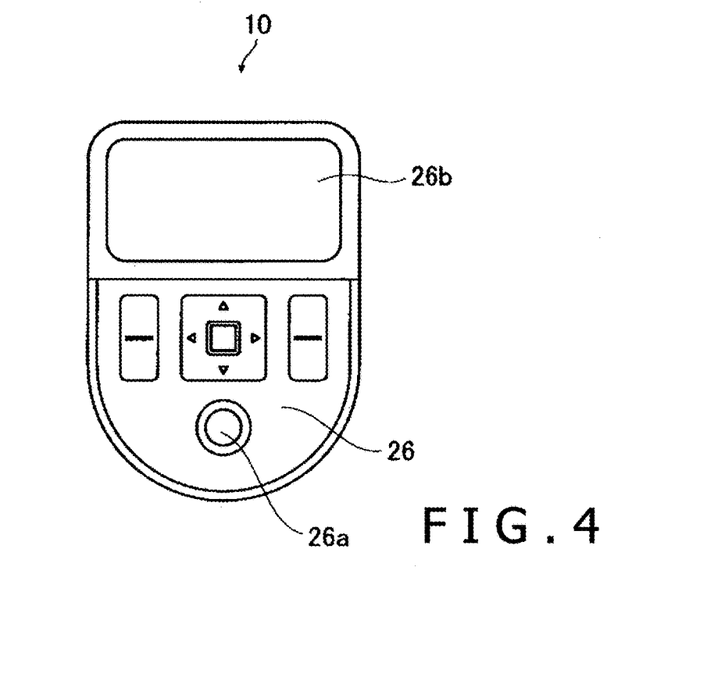
FIG. 4 is a diagram of the automatic injection device shown in FIG. 1 as seen from a direction "a."

FIG. 4 is a schematic diagram of the operation unit 26 of the automatic injection device 10 shown in FIG. 1 as seen from a direction "a."

The operation unit 26 is to carry out input operation by an operator. In the example shown in the diagrams, the operation unit 26 has the start button 26a to start operation of the automatic injection device 10 and a display unit 26b that displays input values and so forth in addition to a cross key for input of operating conditions, an enter button, etc.

Note that the configuration of the operation unit 26 is not limited thereto and the operation unit 26 may have a trackball or the like or may be formed of a touch panel.

The operation unit 26 supplies an input signal to the control unit 22 in accordance with input operation.

In the example shown in the diagrams, the configuration is employed in which the puncture speed, the puncture depth, the size of a mounted syringe, the infusion rate of a drug solution, the infusion amount of the drug solution, and the stop time after drug solution infusion are input from the operation unit 26 as operating conditions. However, the present invention is not limited thereto.

For example, a configuration in which only the puncture speed is input may be employed and the puncture depth, the infusion rate of a drug solution, the infusion amount of the drug solution, and the stop time after drug solution infusion may be set in advance.

Furthermore, the present invention is not limited also to the configuration in which the puncture speed is directly input and a configuration may be employed in which at least one of the thickness of the syringe needle 74, the kind of drug solution, the puncture depth, the infusion amount of the drug solution, and the puncture site is input from the operation unit 26 and the control unit 22 automatically selects the optimum puncture speed according to the input value.

The control unit 22 controls the respective units of the automatic injection device 10 based on an instruction input from the operation unit 26 by an operator.

In the present embodiment, the control unit 22 controls the first drive unit 16 according to puncture speed, puncture depth, stop time, and withdrawal speed input and set from the operation unit 26 and controls the second drive unit 18 according to set infusion rate and infusion amount.

Furthermore, the control unit 22 has a memory to store operating conditions such as the set puncture speed and controls the respective units of the automatic injection device 10 according to the operating conditions stored in the memory. Moreover, if a new operating condition is input from the operation unit 26, the operating condition stored in the memory is overwritten and the automatic injection device 10 is controlled with the new operating condition. In addition, if no input is made, the control is carried out with the operating conditions already stored in the memory.

The battery 28 supplies power to the respective units of the automatic injection device 10, such as the first motor 32, the second motor 40, the control unit 22, and the display unit 26b.

As shown in FIGS. 2 and 3, the housing 12 is a casing that has a substantially cylindrical shape and houses and supports the first drive unit 16, the second drive unit 18, the syringe holder 20, the control unit 22, and the battery 28 inside it.

The first drive unit 16 and the second drive unit 18 are each disposed in the housing 12 with the drive direction (axial direction of the screw shaft (34a, 42a)) set identical to the longitudinal direction of the housing 12. Furthermore, in one end surface of the housing 12, an insertion hole 12a into which the syringe needle 74 is inserted when the syringe 70 is made to advance is formed. Moreover, the part at which the insertion hole 12a is formed in the housing 12 serves as an abutting surface 12b that abuts against a puncture-target site such as the skin across its outer surface. In administration of a drug solution by the automatic injection device 10, after the operating conditions are checked, the abutting surface 12b is made to abut against a puncture-target site such as the skin and the administration operation is started. Therefore, the length of the part protruding from the insertion hole 12a in the distal end of the syringe needle 74 is directly the puncture depth.

Furthermore, the operation unit 26 is disposed on the end surface of the housing 12 on the opposite side to the abutting surface 12b.

Note that the operation unit 26 is disposed with an inclination relative to the abutting surface 12*b* of the housing 12 in the example shown in the diagrams. Disposing the operation unit 26 with an inclination facilitates viewing of the display unit 26*b* of the operation unit 26 when a patient operates the automatic injection device 10.

Furthermore, part of the circumferential surface of the housing 12 is opened and the cover 14 is openably/closably disposed at the open part. In the example shown in the diagrams, the housing 12 and the cover 14 are openably/closably connected by a hinge.

In addition, holding parts 14*a* are formed on the inside surface of the cover 14. When the cover 14 is closed, the holding parts 14*a* suppress the movement of the syringe barrel 72 of the syringe 70 in directions other than the longitudinal direction of the syringe 70 and prevent the syringe 70 from breaking away from the syringe holder 20.

Next, the operation of the automatic injection device 10 will be described.

Figure 5A:
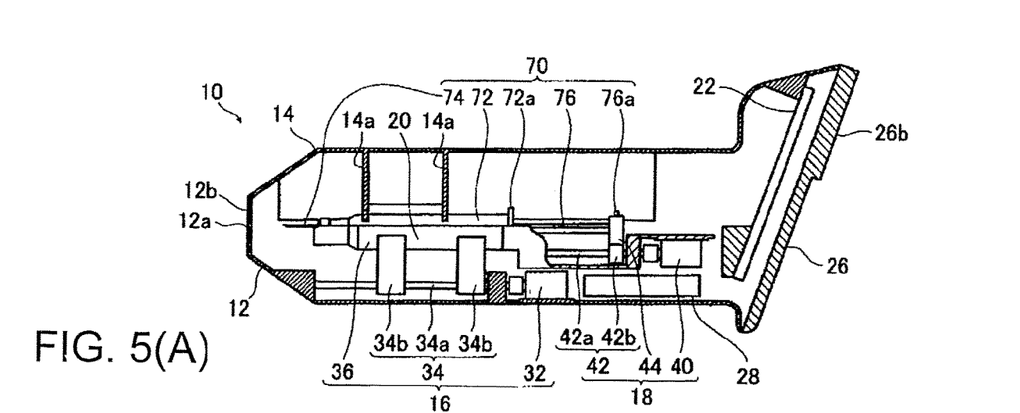
FIGS. 5(A) to 5(C) are diagrams for explaining the operation of the automatic injection device of the present invention.
Figure 5B:
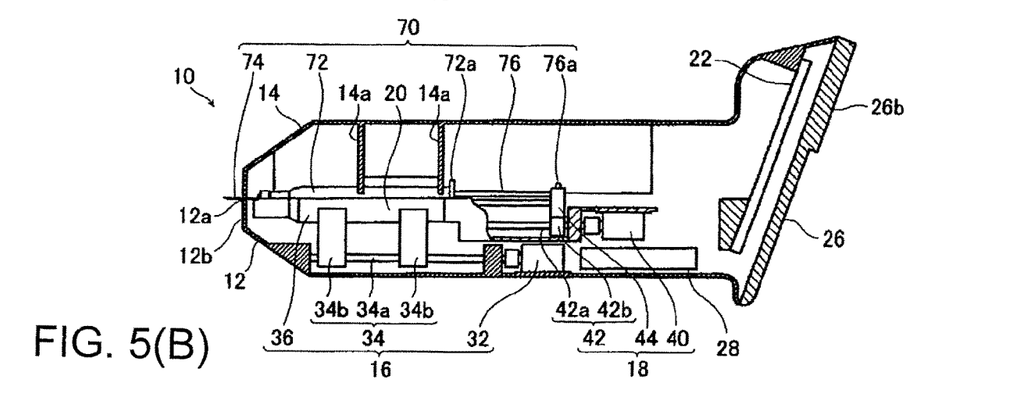
Figure 5C:
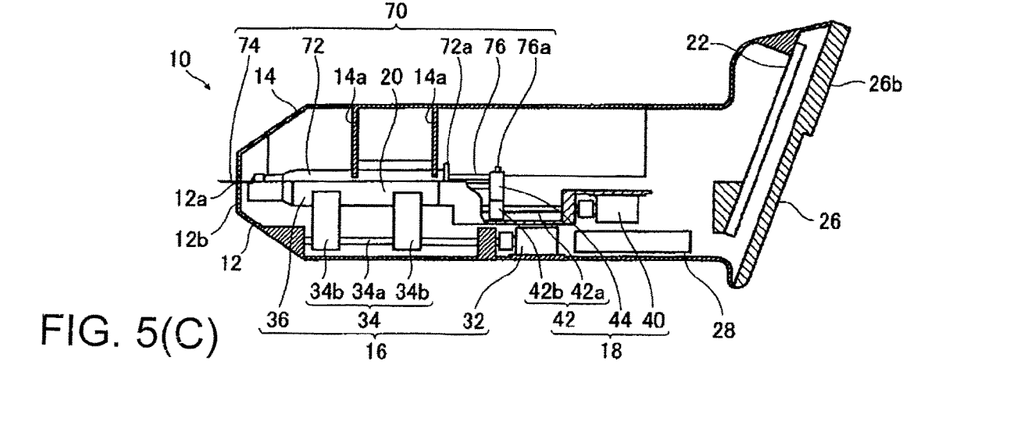

FIGS. 5(A) to 5(C) are schematic sectional views for explaining the operation of the automatic injection device 10.

First, the cover 14 is opened and the syringe 70 with the syringe barrel 72 filled with a drug solution is set on the syringe holder 20, followed by closing of the cover 14 (FIG. 5(A)). At this time, if necessary, position adjustment of the syringe holder 20 (distal end of the syringe needle 74) is carried out by operating the operation unit 26.

Next, the puncture speed, the puncture depth, the infusion rate of the drug solution, and so forth are input and set from the operation unit 26 (stored in the memory). Note that these operating conditions may be set in advance.

The abutting surface 12*b* in which the insertion hole 12*a* is formed in the automatic injection device 10 is pressed against an injection site of a patient and the start button 26*a* of the operation unit 26 is pushed. Thereupon, based on control by the control unit 22, first the first drive unit 16 operates according to the set puncture speed and puncture depth to cause the syringe holder 20 and the second drive unit 18 to advance to a predetermined position (FIG. 5(B)). Thereby, the syringe needle 74 of the syringe 70 held by the syringe holder 20 protrudes from the insertion hole 12*a* and punctures the injection site of the patient.

Here, the first drive unit 16 is composed of the first motor 32 and the first motion converter 34 and is so configured that operating conditions can be set. Thus, the puncture can be performed by making the syringe holder 20 advance at the set puncture speed and the puncture can be performed at a proper puncture speed depending on the thickness of the syringe needle, the puncture depth, the patient, and so forth. This reduces pain in the puncture and reduces the impact in the puncture, allowing alleviation of anxiety and fear of the patient.

Furthermore, because the first drive unit 16 to perform the puncture is configured independently of the second drive unit 18 to infuse the drug solution, a proper puncture speed (puncture condition) can be set regardless of operating conditions of the second drive unit 18.

After the puncture operation by the first drive unit 16, the first drive unit 16 temporarily stops the operation and the second drive unit 18 makes the pressing member 44 advance to infuse a predetermined amount of drug solution at the set infusion rate based on control by the control unit 22 (FIG. 5(C)).

Upon the end of the infusion operation of the drug solution by the second drive unit 18, after the elapse of a predetermined stop time, the control unit 22 actuates the first drive unit 16 to cause the syringe holder 20 and the second drive unit 18 to retreat to the original position and withdraw the syringe needle 74 from the patient.

Note that an indication showing the operation end may be displayed on the display unit 26*b* or the completion may be informed by sound after the end of the withdrawal operation of the first drive unit 16.

In the above-described manner, the automatic injection device 10 according to the present invention can automatically perform the puncture with the syringe needle 74, the infusion of a drug solution, and the withdrawal of the syringe needle 74.

Here, in the automatic injection device 10 of the example shown in the diagrams, the configuration is employed in which the second drive unit 18 is placed on the base 36 of the first drive unit 16 and moves integrally with the syringe holder 20. However, the present invention is not limited thereto and a configuration in which the second drive unit 18 is fixed to the housing 12 may be employed.

When the configuration in which the second drive unit 18 is fixed to the housing 12 is employed, the second drive unit 18 moves the pressing member 44 at the same speed as the advance speed (or retreat speed) of the syringe holder 20 in the movement of the syringe holder 20 by the first drive unit 16 for example.

Specifically, first, in the puncture operation by the first drive unit 16, the second drive unit 18 makes the pressing member 44 advance at the same speed as the puncture speed simultaneously with the operation of the first drive unit 16. Next, the second drive unit 18 makes the pressing member 44 advance to infuse a drug solution at a predetermined infusion rate during the stop of the operation of the first drive unit 16. After the elapse of a predetermined stop time, in withdrawal operation by the first drive unit 16, the second drive unit 18 makes the pressing member 44 retreat at the same speed as the withdrawal speed simultaneously with the operation of the first drive unit 16.

Alternatively, as another example of the configuration in which the second drive unit 18 is fixed to the housing 12, a configuration may be employed in which the locking groove 44*a* is not formed in the pressing member 44 and the pressing member 44 only presses the flange 76*a* of the plunger 76 and is not locked.

In this case, after the syringe holder 20 on which the syringe 70 is placed moves and puncture is performed by the first drive unit 16, the second drive unit 18 moves the pressing member 44 to the position of the flange 76*a* of the plunger 76 and then makes the pressing member 44 advance to infuse a drug solution at a predetermined infusion rate. Thereafter, the second drive unit 18 makes the pressing member 44 retreat to the original position and then withdrawal operation by the first drive unit 16 is carried out.

When the configuration in which the second drive unit 18 is fixed to the housing 12 and does not move is employed as above, the mass of the moving object moved by the first drive unit 16 becomes lighter and thus recoil in puncture becomes smaller. Furthermore, the output power of the first motor 32 can be decreased and weight reduction can be achieved by using a small-size motor.

On the other hand, when the configuration is employed in which the second drive unit 18 is placed on the base 36 of the first drive unit 16 and moves integrally with the syringe holder 20, control of the operation can be simplified.

Furthermore, although the configuration in which a drug solution is automatically infused by the second drive unit 18 is employed in the example shown in the diagrams, the present invention is not limited thereto and a configuration in which only puncture operation by the first drive unit 16 is automatically carried out may be employed as a configuration in which the automatic injection device 10 does not have the second drive unit 18. For example, when a drug solution is applied on the syringe needle 74 to be administered, it is enough to automatically perform only puncture. Alternatively, a configuration in which only puncture is automatically performed and a drug solution is manually infused by an operator may be employed.

In addition, in the example shown in the diagrams, the configuration is employed in which the cover 14 has the holding parts 14a and the holding parts 14a hold the syringe 70 to prevent the syringe 70 from breaking away from the syringe holder 20. However, the configuration is not limited thereto and a configuration in which the syringe holder 20 has a fixing instrument for fixing the syringe 70 may be employed.

Moreover, in the present embodiment, the configuration is employed in which the first drive unit 16 makes the syringe holder 20 retreat to carry out withdrawal operation of the syringe needle 74 after the elapse of a predetermined stop time after infusion operation of a drug solution by the second drive unit 18. However, the configuration is not limited thereto and the following configuration may be employed. Specifically, the time from the completion of puncture by the syringe needle 74 through an advance of the syringe holder 20 by the first drive unit 16 is treated as the predetermined stop time and the first drive unit 16 makes the syringe holder 20 retreat to carry out withdrawal operation of the syringe needle 74 after the elapse of the predetermined stop time from the puncture completion.

Furthermore, the present invention is not limited also to the configuration in which the first drive unit 16 carries out withdrawal operation after the elapse of the predetermined stop time and the following configuration may be employed. Specifically, the infusion pressure relating to drug solution infusion by the second drive unit 18 is measured and the withdrawal operation by the first drive unit 16 is carried out when the infusion pressure has become equal to or lower than a predetermined threshold.

Specifically, a pressure sensor to measure the pressure applied from the plunger 76 is disposed to the pressing member 44 and the pressure applied to the pressure sensor is measured. Because it takes a certain amount of time for a drug solution infused into a body to diffuse in the body, the pressure applied from the drug solution to the plunger 76 is high immediately after the infusion of the drug solution. As time passes, the drug solution diffuses in the body and the pressure applied from the drug solution to the plunger 76 gradually decreases. Therefore, by carrying out withdrawal operation by the first drive unit 16 when the infusion pressure measured by the pressure sensor has become equal to or lower than a predetermined threshold, the leakage of the drug solution when the syringe needle 74 is withdrawn can be prevented. Furthermore, pressure abnormality occurs if a drug solution is not infused to a predetermined site in a hypodermis, muscle, or blood vessel but accidentally infused into different tissue. Thus, erroneous administration can be forestalled by sensing the abnormality.

In addition, in the example shown in the diagrams, the distal portion including the insertion hole 12a, into which the syringe needle 74 is inserted, is monolithically formed in the housing 12. However, the present invention is not limited thereto and the distal portion including the insertion hole 12a may be replaceably configured as a separate member.

The distal portion of the housing 12 is a part that gets contact with an injection site of a patient and the syringe needle 74 is inserted through it. Thus, there is a possibility that a leaked drug solution and blood by bleeding attach to the distal portion and there is a fear that infection or the like becomes a problem. Therefore, by replaceably configuring the distal portion including the insertion hole 12a as a separate member from the housing 12, the distal portion, which gets contact with an injection site of a patient, can be kept clean and infection or the like can be prevented.

Moreover, in the above-described embodiment, the configuration is employed in which an operator manually carries out position adjustment of the distal end position of the syringe needle 74 in setting the syringe 70 in the automatic injection device 10 by operating the operation unit 26. However, the present invention is not limited thereto and a configuration in which the distal end position of the syringe needle 74 is automatically adjusted may be employed. For example, a configuration may be employed in which an optical sensor is disposed at the distal part in the housing 12 to measure the distal end position of the syringe needle 74 and the first drive unit 16 is made to cause advance/retreat to carry out position adjustment according to the measurement result.

Note that there is no particular limit to the range of the position (distance from the abutting surface 12b (insertion hole 12a) of the housing 12) of the distal end of the syringe needle 74 in the state in which the syringe 70 is set in the automatic injection device 10. However, it is preferable for the distal end to have a sufficient distance to accelerate the syringe needle 74 to a set puncture speed by the time when the distal end of the syringe needle 74 reaches the skin surface of a patient and puncture is started, according to the performance of the first drive unit 16, the mass of the syringe holder 20 and the second drive unit 18, and so forth.

Furthermore, in the example shown in the diagrams, the configuration is employed in which the first drive unit 16 is controlled by the control unit 22 to perform puncture at a set constant puncture speed. However, the present invention is not limited thereto and the puncture speed may be changed in the middle of puncture. For example, the puncture speed may be variably controlled in such a manner that puncture is performed at a high puncture speed until reaching a skin's dermis layer and is then performed at a low puncture speed after that.

In addition, in the case of using such an automatic injection device, the syringe 70 in which the same kind of drug solution is housed is used for one patient basically. Therefore, it is enough that initially operating conditions such as the puncture speed, the puncture depth, the infusion amount of a drug solution, and the stop time are set and there is no need to set the operating conditions in every injection.

Moreover, a configuration may be employed in which the automatic injection device 10 has a detailed setting mode in which operating conditions such as the puncture speed, the puncture depth, the infusion amount of a drug solution, the infusion rate, and the stop time can be set in detail in making input from the operation unit 26 and a simple setting mode in which only the puncture speed can be set. The following way may be employed. Specifically, when the automatic injection device is used for the first time, a doctor sets the operating conditions in detail in the detailed setting mode. In the subsequent injections, only the puncture speed is set again in the simple setting mode depending on the patient's preference. Furthermore, the setting of the puncture speed in the simple setting mode is not limited to numerical value input. For example, the puncture speed may be set through choice from puncture speeds set in advance at five stages by an indication of "1" to "5" or the like.

Furthermore, in the above-described embodiment, the automatic injection device 10 is made to directly abut against a puncture site across the abutting surface 12b. However, it is enough that the distance between the syringe needle 74 and the puncture site can be identified and a fixing auxiliary instrument to settle the relative positions of the puncture site and the syringe needle 74 may be disposed between the automatic injection device 10 and the puncture site.

WORKING EXAMPLES

Next, the range of a preferred puncture speed will be described in more detail by using working examples.

The inventors of the present application have found that following facts. Specifically, in puncture by a syringe needle, the penetration resistance decreases depending on the puncture speed. In addition, suppression of the pain response is found in rat electromyography and the pain response evoked by puncture disappears if the puncture speed is higher than a certain puncture speed. Although what kind of behavior causes such an effect in pain sensing nerves of the skin is unclear, due to the high-speed puncture, an action potential would not be generated in the Na ion channel, the Ca ion channel, and so forth to transmit excitement for stimulating nerve terminals that are the pain sensing nerves of the skin.

Therefore, the inventors of the present application made a puncture device that could perform puncture similar to that by the automatic injection device 10 and measured the relationship among the puncture speed, the penetration resistance, and electromyography by using this puncture device to obtain the range of a preferred puncture speed with which no pain response was evoked.

Figure 6:
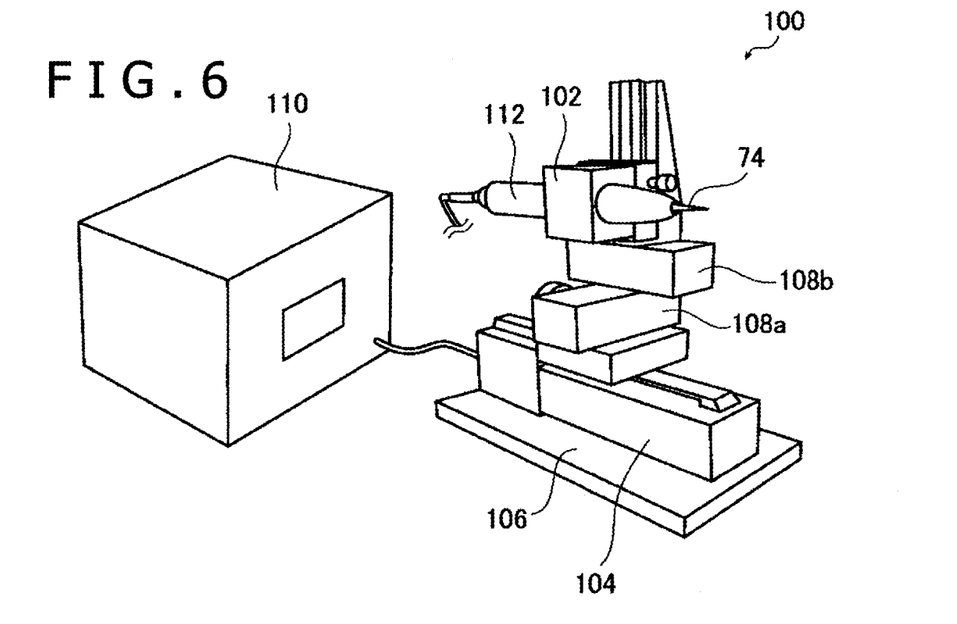
FIG. 6 is a perspective view conceptually showing another example of the automatic injection device of the present invention.

In FIG. 6, a puncture device 100 is shown.

The puncture device 100 is an experimental device fabricated to obtain the relationship between the puncture speed and the electromyography response. It is so configured that various syringe needles can be mounted at the tip and the puncture depth, the puncture speed, the withdrawal speed, and so forth can be set. It performs puncture at the set puncture speed. Note that this puncture device 100 has functions similar to those of the device according to the present invention basically.

The puncture device 100 has the following components: a holder 102 that holds a load cell 112 to which the syringe needle 74 is attached at the tip; a linear actuator 104 that makes the holder 102 advance to perform puncture; an X-table 108a and a Z-table 108b that are disposed between the holder 102 and the linear actuator 104 and are to adjust the position of the holder 102; a controller 110 that controls operation of the linear actuator 104; and a base 106 on which to place the linear actuator 104.

Here, the linear actuator 104 is composed of a stepping motor and a ball screw.

In the puncture device 100, the controller 110 makes the linear actuator 104 advance at a set puncture speed to perform puncture.

Working Example 1

As working example 1, puncture was performed in the plantar regions of rats by using the puncture device 100.

The puncture speed of the puncture device 100 was set to 3 mm/s. The puncture depth was set to 3 mm. The stop time was set to two seconds. The withdrawal speed was set to 20 mm/s.

Furthermore, as the syringe needle 74, a syringe needle with a thickness of 27 G (27 G Neolus needle φ0.40×19 mm, made by Terumo Corporation) was used.

In addition, the distance between the tip of the syringe needle 74 before operation start and a puncture site was set to 3 mm. That is, a configuration in which the puncture device 100 made the syringe needle advance by 6 mm was employed.

Moreover, as the rats of the puncture subject, 7- to 8-week-old SD male rats were purchased from Charles River Laboratories Japan, Inc. and were used for the experiment after an acclimatization period of one week was set. The weights of the animals at the time of the experiment were 273 g to 314 g.

The rats were anesthetized by inhalation of isoflurane (Escain made by Mylan Inc.). The concentration relative to air in anesthesia induction was set to 4%/Air and the concentration in recording and measurement was set to 1.4 to 1.6%/Air. Furthermore, during the anesthesia, the temperature was heated to 42° C. by a keep-warm mat to keep the body temperature constant.

Under such conditions, puncture was performed by using the puncture device 100 and the muscle action potential and the penetration resistance were measured. For the measurement, on six rats, each plantar region was punctured total four times with slight offsets of the puncture position. Note that the needle was replaced in each use.

As the load cell 112, a micro load cell (RX-1/CPM-N made by Aikoh Engineering Co., Ltd.) was used to measure the penetration resistance.

Furthermore, as the state of the puncture, how the syringe needle 74 was inserted into the rat plantar skin was observed at a rate of 4000 frames/second by using a high-speed microscope (VW-9000 made by Keyence).

A marking was made at a position of 3 mm from the tip of the syringe needle 74 so that the position of insertion into the skin could be discriminated. The movement distance of the needle per unit time was measured from high-speed microscope images and the actual puncture speed was calculated.

Figure 7:
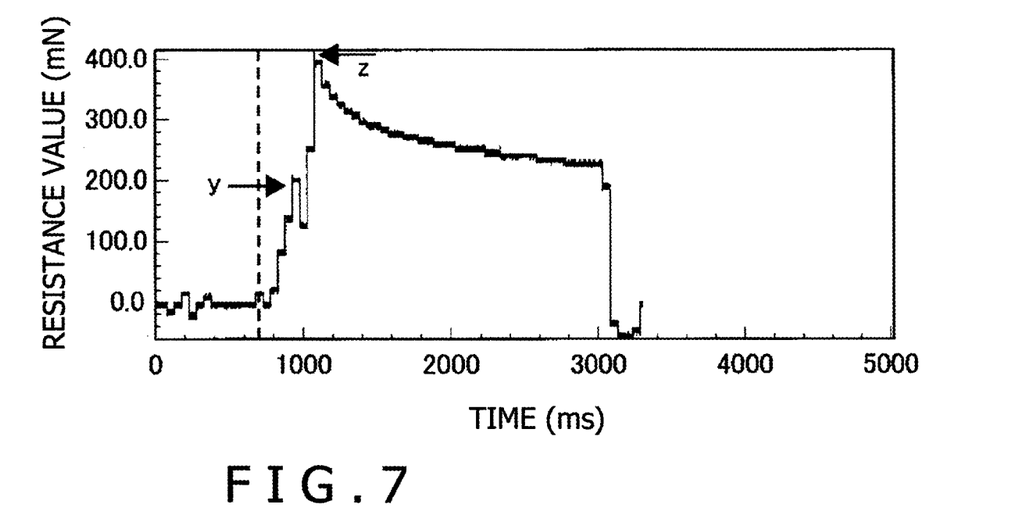
FIG. 7 is a graph representing a result of measurement of the penetration resistance in puncture.

In FIG. 7, a graph of the penetration resistance measured when puncture with the 27 G needle was performed at a puncture speed of 15 mm/s is shown. Here, in FIG. 7, the abscissa is defined as the time [ms] and the ordinate is defined as the resistance value (penetration resistance) [mN]. Furthermore, the time when the tip of the syringe needle 74 got contact with the skin was read from high-speed microscope images and is indicated by a dotted line in FIG. 7. Similarly, the time when a jaw portion of the bevel of the syringe needle 74 reached the skin surface was read and is indicated by an arrow y in FIG. 7, and the time when the puncture with the syringe needle 74 ended (timing of a puncture depth of 3 mm) was read and is indicated by an arrow z in FIG. 7.

Figure 8A:
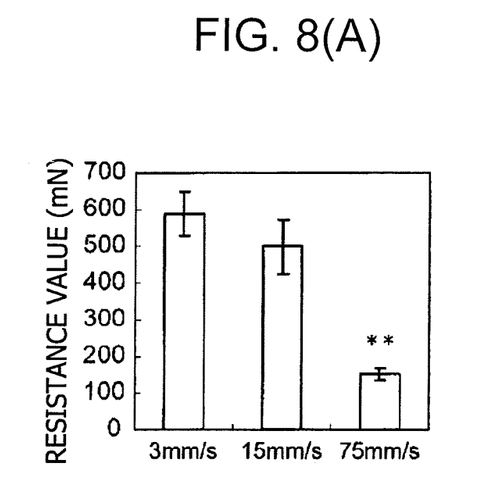
FIG. 8(A) is a graph showing the relationship between the puncture speed and the penetration resistance.

Furthermore, the resistance value at the timing when the puncture with the syringe needle 74 ended (puncture depth was 3 mm) (arrow z) is shown in FIG. 8(A).

Furthermore, for recording of the muscle action potential (hereinafter, referred to also as the electromyography), a needle-shaped bipolar electrode was employed as a recording electrode and an aluminum foil as an earth electrode was attached to the breast skin after dehairing. After amplification by a factor of twenty thousand by a high-sensitivity bioelectric amplifier (ER-1 Extracelular Amplifier made by CYGNUS TECHNOLOGY Inc.), an action potential waveform was displayed on a screen of a personal computer through PowerLab 16/30 (made by ADInstruments). Note that low-pass filter and high-pass filter of the high-sensitivity bioelectric amplifier were set to 3 kHz and 300 Hz, respectively, in order to minimize noise in the potential measurement.

Furthermore, to facilitate evocation of the paw withdrawal reflex (spinal reflex), the rat was retained with the paw stretched as much as possible.

Before incision of the thigh skin, to check muscle contraction, a clip-type stimulating electrode (TH207-123 made by Unique Medical) was used to clamp the dorsum and sole of the rat hind paw and pain electrical stimuli (pulse conditions: 40 Hz, 2 ms, 5 mA) were given by an electrostimulator (BSI-950 Biphasic Stimulus Isolator made by Dagan Corporation).

A line of about 1 cm was drawn at the contracted muscle part and the part was incised. The muscle was exposed and the pain electrical stimuli were given again, and the recording electrode probe was surely indwelled at the contracted muscle part. Thereafter, the pain electrical stimuli were performed again and the anesthetic depth of the rat was fine-tuned from the response strength of the electromyography action potential (maximum amplitude value).

The muscle action responses evoked by electrical stimuli and pressure stimuli were recorded in a recording device (PowerLab made by ADInstruments) at a sampling interval of 0.1 ms.

The recorded data was subjected to 30-Hz high-pass digital filter processing in the recording device to remove the influence of body motion caused by the electrical stimuli and pressure stimuli.

Regarding the recorded data of the muscle action potential, after the data was subjected to full-wave rectification, the position of insertion of the needle into the skin was checked by the high-speed microscope and the range from the point at which the needle tip got contact with the skin (insertion start) to the point at which the needle tip was inserted by 3 mm (insertion stop) was integrated to calculate the electromyography (EMG) response magnitude as Total Power ($\mu V \cdot sec$). The value of integral of the action potential was obtained based on a method by Ando et al. (Ando R, et al., Br. J. Anaesth., 95:384, 2005).

Figure 8B:
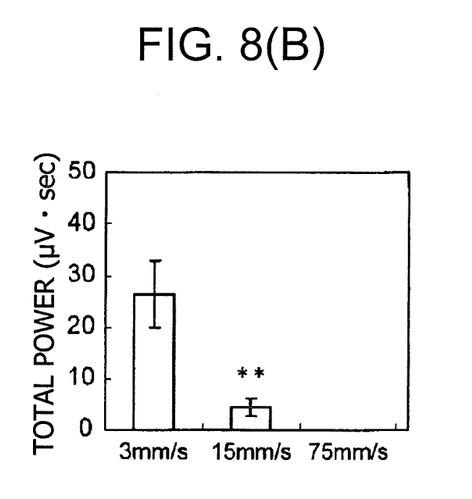
FIG. 8(B) is a graph showing the relationship between the puncture speed and the electromyography response magnitude.

In FIG. 8(A), the resistance value when puncture with the 27 G needle was performed at a puncture speed of 3 mm/s is shown. In FIG. 8(B), the measured EMG response magnitude (Total Power) is shown. Note that, in FIG. 8(A), the average and standard error of the measured resistance value are shown. Similarly, in FIG. 8(B), the average and standard error of the measured Total Power are shown.

Here, although the EMG response magnitude was measured by using rats in the present working example, the human body would also show a tendency similar to that of the rat basically.

Working Example 2

Except for that the puncture speed was changed to 15 mm/s, the penetration resistance and the EMG response magnitude were obtained similarly to working example 1.

The resistance value at the timing when the puncture with the syringe needle 74 ended (puncture depth was 3 mm) (arrow z) is shown in FIG. 8(A) and the EMG response magnitude (Total Power) is shown in FIG. 8(B).

Working Example 3

Except for that the puncture speed was changed to 75 mm/s, the penetration resistance and the EMG response magnitude were obtained similarly to working example 1.

The resistance value at the timing when the puncture with the syringe needle 74 ended (puncture depth was 3 mm) (arrow z) is shown in FIG. 8(A) and the EMG response magnitude (Total Power) is shown in FIG. 8(B).

Working Example 4

Except for that the thickness of the syringe needle 74 was changed to 31 G (Microfine Plus $\varphi$ 0.25×5 mm made by Becton, Dickinson and Company), the penetration resistance and the EMG response magnitude were obtained similarly to working example 1.

Figure 9A:
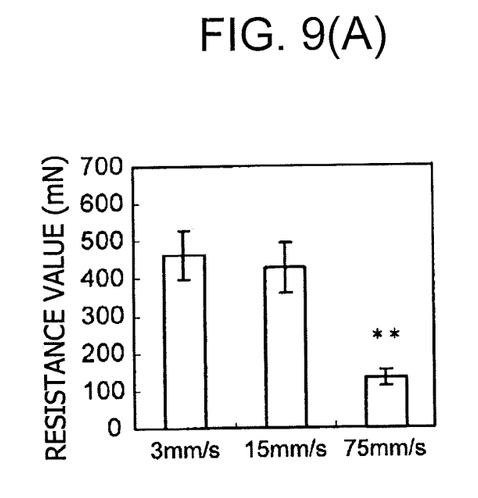
FIG. 9(A) is a graph showing the relationship between the puncture speed and the penetration resistance.
Figure 9B:
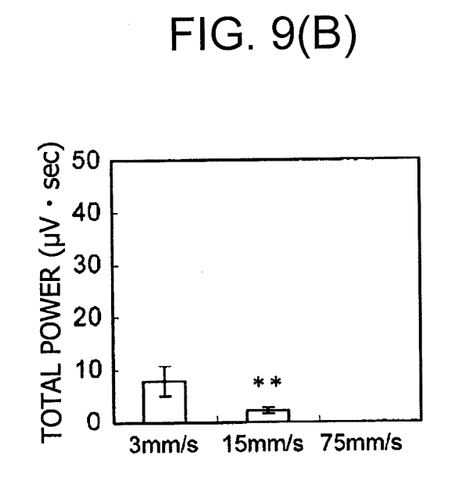
FIG. 9(B) is a graph showing the relationship between the puncture speed and the electromyography response magnitude.

The resistance value at the timing when the puncture with the syringe needle 74 ended (puncture depth was 3 mm) (arrow z) is shown in FIG. 9(A) and the EMG response magnitude (Total Power) is shown in FIG. 9(B).

Working Example 5

Except for that the puncture speed was changed to 15 mm/s, the penetration resistance and the EMG response magnitude were obtained similarly to working example 4.

The resistance value at the timing when the puncture with the syringe needle 74 ended (puncture depth was 3 mm) (arrow z) is shown in FIG. 9(A) and the EMG response magnitude (Total Power) is shown in FIG. 9(B).

Working Example 6

Except for that the puncture speed was changed to 75 mm/s, the penetration resistance and the EMG response magnitude were obtained similarly to working example 4.

The resistance value at the timing when the puncture with the syringe needle 74 ended (puncture depth was 3 mm) (arrow z) is shown in FIG. 9(A) and the EMG response magnitude (Total Power) is shown in FIG. 9(B).

As shown in FIG. 7, it turns out that the resistance value of the penetration resistance increased as the syringe needle 74 was inserted into the skin to a deeper position and showed the first peak (arrow y) when the jaw portion of the bevel reached the skin. It turns out that, thereafter, the resistance value temporarily decreased and then increased again as the cannula part of the needle went into a deeper position to show the maximum value at the timing of stop of the puncture (puncture depth was 3 mm, arrow z). It turns out that, thereafter, the resistance value remained near a certain value during the stop of the movement of the syringe needle 74 (for two seconds) and rapidly decreased when withdrawal of the syringe needle 74 was started and the resistance value returned to the basal level upon the completion of the withdrawal.

Furthermore, from FIGS. 8(A) and 9(A), it turns out that the resistance value in the puncture was lower with the 31 G syringe needle than with the 27 G needle, i.e. lower when the thickness of the syringe needle was smaller, regardless of the puncture speed.

Moreover, it turns out that the resistance value in the puncture became lower in proportion to the puncture speed as the puncture speed became higher in both cases of the 27 G and 31 G syringe needles.

Note that FIG. 8 shows the resistance value and the EMG response magnitude of 27 G, and FIG. 9 shows the resistance value and the EMG response magnitude of 31 G.

Furthermore, from FIGS. 8(B) and 9(B), it turns out that the EMG response magnitude with the thickness 31 G of the syringe needle 74 was half or smaller compared with that with the thickness 27 G when the puncture speed was 3 mm/s or 15 mm/s.

In addition, it turns out that, when the puncture speed was set to 15 mm/s, the EMG response magnitude greatly decreased compared with that when the puncture speed was 3 mm/s in both cases of the thicknesses 31 G and 27 G of the syringe needle 74. Moreover, when the puncture speed was set to 75 mm/s, the EMG response did not appear at all regardless of the thickness of the syringe needle 74.

The measurement values were shown by the average and the standard error when puncture was performed four times on each of the six rats, and a statistical significance test was performed by using one-way analysis of variance (**: $p<0.01$).

From the above results, it turns out that, when the thickness of the syringe needle is in a range of 18 G to 34 G, setting the puncture speed equal to or higher than 10 mm/s can greatly decrease the EMG response magnitude and allows puncture with almost no pain felt. Furthermore, it turn out that setting the puncture speed equal to or higher than 25 m/s can make the EMG response almost zero and allows almost painless puncture. Moreover, it turns out that setting the puncture speed equal to or higher than 75 m/s can avoid generation of the EMG response and allows sure painless puncture.

Although the automatic injection device of the present invention is described in detail above, the present invention is not limited to the above-described embodiment and various kinds of improvements and changes may be made without departing from the scope of the present invention.

DESCRIPTION OF REFERENCE SYMBOLS

10 Automatic injection device
12 Housing
12a Insertion hole
12b Abutting surface
14 Cover
14a Holding part
16 First drive unit
18 Second drive unit
20 Syringe holder
20a Recess
20b Locking groove
22 Control unit
26 Operation unit
26a Start button
26b Display unit
28 Battery
32 First motor
34 First motion converter
34a, 42a Screw shaft
34b, 42b Block
34c, 42c Guide shaft
36 Base
40 Second motor
42 Second motion converter
44 Pressing member
70 Syringe
72 Syringe barrel
72a, 76a Flange
74 Syringe needle
76 Plunger
100 Puncture device
102 Holder
104 Linear actuator
106 Base
108a X-table
108b Z-table
110 Controller
112 Load cell

What is claimed is:

1. A method for measuring an amount of pain comprising:
   positioning a needle adjacent a non-human animal which is under anesthesia;
   automatically inserting the needle at a controlled puncture speed into skin of the non-human animal by an automatic needle puncture device; and
   measuring a muscle action potential of a muscle portion of the non-human animal produced by the insertion of the needle, the muscle action potential being measured from insertion start, at which the insertion of the needle into the skin is started, to insertion stop, at which the insertion of the needle into the skin is stopped,
   whereby the measured muscle action potential indicates a measurement of the amount of pain.

2. The method for measuring an amount of pain according to claim 1, the method further comprising determining a Total Power ($\mu V \cdot sec$) by integrating the measured muscle action potential from the insertion start to the insertion stop, the Total Power indicating the amount of pain associated with the insertion of the needle into the non-human animal.

3. The method for measuring an amount of pain according to claim 1, further comprising observing a condition of the puncture needle using a high-speed microscope, and measuring movement distance of the needle per unit time from images produced by the high-speed microscope.

4. The method for measuring an amount of pain according to claim 3, further comprising measuring a position of insertion of the needle into the skin of the non-human animal using a mark of the needle determined from the images produced by the high-speed microscope.

5. The method for measuring an amount of pain according to claim 1, wherein the non-human animal is anesthetized by inhalation of isoflurane having a concentration relative to air of 1.4 to 1.6%/Air.

6. The method for measuring an amount of pain according to claim 1, further comprising controlling a depth of insertion of the needle into the skin of the non-human animal up to the insertion stop of the needle.

7. The method for measuring an amount of pain according to claim 1, further comprising amplifying the muscle action potential, for measuring the muscle action potential, through use of a bioelectric amplifier.

8. The method for measuring an amount of pain according to claim 1, further comprising, before the insertion of the needle:
   positioning two stimulating electrodes on the skin of the non-human in spaced apart relation to one another;
   applying a pain electrical stimuli to the skin through the electrodes; and
   checking the muscle portion contracted by the stimuli to observe muscle movement.

9. The method for measuring an amount of pain according claim 8, wherein the muscle action potential is measured when the pain electrical stimuli is applied and an anesthetic depth of the animal is fine-tuned from a response strength of electromyography action potential.

* * * * *